(12) United States Patent
Reinauer et al.

(10) Patent No.: US 9,700,335 B2
(45) Date of Patent: Jul. 11, 2017

(54) SURGICAL GRIPPING FORCEPS

(75) Inventors: Josef Reinauer, Sigmaringen (DE); Hans Ganter, Tuttlingen (DE)

(73) Assignee: KARL STORZ GMBH & CO. KG, Tuttlingen (DE)

( * ) Notice: Subject to any disclaimer, the term of this patent is extended or adjusted under 35 U.S.C. 154(b) by 1412 days.

(21) Appl. No.: 12/438,359

(22) PCT Filed: Aug. 23, 2007

(86) PCT No.: PCT/EP2007/007412
§ 371 (c)(1),
(2), (4) Date: Jun. 15, 2009

(87) PCT Pub. No.: WO2008/025480
PCT Pub. Date: Mar. 6, 2008

(65) Prior Publication Data
US 2010/0023050 A1     Jan. 28, 2010

(30) Foreign Application Priority Data
Aug. 30, 2006 (DE) .................. 10 2006 040 529

(51) Int. Cl.
*A61B 17/29* (2006.01)
(52) U.S. Cl.
CPC ...... *A61B 17/29* (2013.01); *A61B 2017/2931* (2013.01); *A61B 2017/2936* (2013.01); *A61B 2017/2939* (2013.01)
(58) Field of Classification Search
CPC ............ A61B 17/29; A61B 2017/2939; A61B 2017/2931; A61B 2017/2936;
(Continued)

(56) References Cited

U.S. PATENT DOCUMENTS 4,887,612 A * 12/1989 Esser ................... A61B 10/06
                                                                                      294/116
5,147,357 A *  9/1992 Rose .................... A61B 17/29
                                                                                       606/49

(Continued)

FOREIGN PATENT DOCUMENTS

DE      10056238         5/2002
DE      10316132        10/2003
(Continued)

OTHER PUBLICATIONS

International Search Report for PCT No. PCT/EP2007/007412 Filed Aug. 23, 2007, 12 pages with translation of Examiner comments.

*Primary Examiner* — Ryan J Severson
(74) *Attorney, Agent, or Firm* — Andrew F. Young, Esq.; Lackenbach Siegel, LLP

(57) ABSTRACT

Surgical gripping forceps are provided with one or two gripping jaws movable relative to a main body, wherein each moveable one of the gripping jaws has a pivot pin, fixed in position relative to the main body, and a lever arm. The lever arms are articulated via at least one push element. For this purpose each movable one of the gripping jaws has its own pivot pin. From the midline of the main body, the individual pivot pin has at least a distance greater than 38% of the maximum width of the main body or maximum diameter of the main body. The microsurgical gripping forceps operate with customary force for actuating the forceps, and permit a substantial applied clamping force.

23 Claims, 5 Drawing Sheets

(58) Field of Classification Search
CPC .... A61B 2017/2926; A61B 2017/2932; A61B 2017/2933; A61B 2017/294; A61B 2017/2941
USPC .................................................. 606/205–207
See application file for complete search history.

(56) References Cited

U.S. PATENT DOCUMENTS

| | | | | |
|---|---|---|---|---|
| 5,254,130 A * | 10/1993 | Poncet | A61B 17/29 | |
| | | | | 600/564 |
| 5,308,358 A * | 5/1994 | Bond | A61B 17/29 | |
| | | | | 606/170 |
| 5,366,467 A * | 11/1994 | Lynch | A61B 17/320016 | |
| | | | | 606/174 |
| 5,366,477 A * | 11/1994 | LeMarie, III | A61B 17/29 | |
| | | | | 403/336 |
| 5,590,570 A * | 1/1997 | LeMaire, III | A61B 17/29 | |
| | | | | 403/336 |
| 5,649,955 A * | 7/1997 | Hashimoto | A61B 17/29 | |
| | | | | 600/562 |
| 5,947,996 A * | 9/1999 | Logeman | A61B 17/29 | |
| | | | | 600/564 |
| 6,019,780 A * | 2/2000 | Lombardo et al. | 606/207 | |
| 6,063,103 A * | 5/2000 | Hashiguchi | A61B 17/29 | |
| | | | | 606/205 |
| 6,228,082 B1 | 5/2001 | Baker et al. | | |
| 6,599,309 B1 * | 7/2003 | Gilman | A61B 17/1608 | |
| | | | | 606/205 |
| 6,818,005 B2 * | 11/2004 | Kupferschmid | A61B 17/29 | |
| | | | | 279/30 |
| 6,964,662 B2 * | 11/2005 | Kidooka | A61B 18/1442 | |
| | | | | 606/205 |
| 7,211,099 B2 * | 5/2007 | Lang | A61B 17/1608 | |
| | | | | 606/206 |
| 7,708,757 B2 * | 5/2010 | Ganter | A61B 17/2909 | |
| | | | | 606/205 |
| 7,976,563 B2 * | 7/2011 | Summerer | A61B 17/29 | |
| | | | | 606/205 |
| 9,011,484 B2 * | 4/2015 | Reinauer | A61B 17/2909 | |
| | | | | 606/205 |
| 9,072,538 B2 * | 7/2015 | Suzuki | A61B 17/29 | |
| 2003/0135204 A1 * | 7/2003 | Lee | A61B 17/0469 | |
| | | | | 606/1 |
| 2004/0093019 A1 * | 5/2004 | Kothe | A61B 17/29 | |
| | | | | 606/205 |
| 2004/0098038 A1 * | 5/2004 | Lang | A61B 17/1608 | |
| | | | | 606/205 |
| 2006/0047304 A1 * | 3/2006 | Ganter | A61B 17/2909 | |
| | | | | 606/205 |
| 2009/0259248 A1 * | 10/2009 | Ganter | A61B 17/29 | |
| | | | | 606/205 |
| 2010/0023050 A1 * | 1/2010 | Reinauer | A61B 17/29 | |
| | | | | 606/207 |
| 2012/0004684 A1 * | 1/2012 | Reinauer | A61B 17/2909 | |
| | | | | 606/205 |
| 2013/0211446 A1 * | 8/2013 | Reinauer | A61B 17/2909 | |
| | | | | 606/205 |

FOREIGN PATENT DOCUMENTS

| | | |
|---|---|---|
| DE | 60004070 T2 | 4/2004 |
| EP | 1543786 | 6/2005 |
| EP | 2 056 727 | 10/2011 |
| WO | WO98/33436 | 8/1998 |
| WO | WO02/45599 | 6/2002 |
| WO | WO02/064020 | 8/2002 |

* cited by examiner

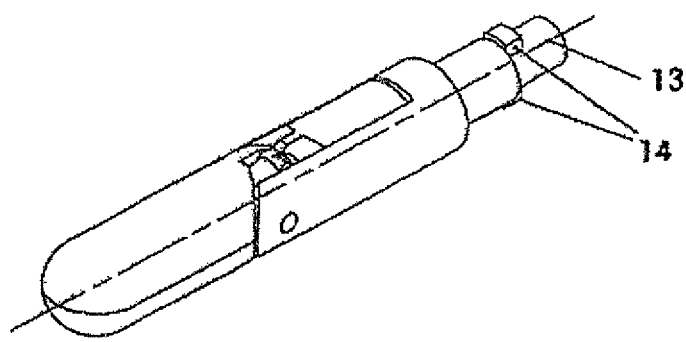
Fig. 1
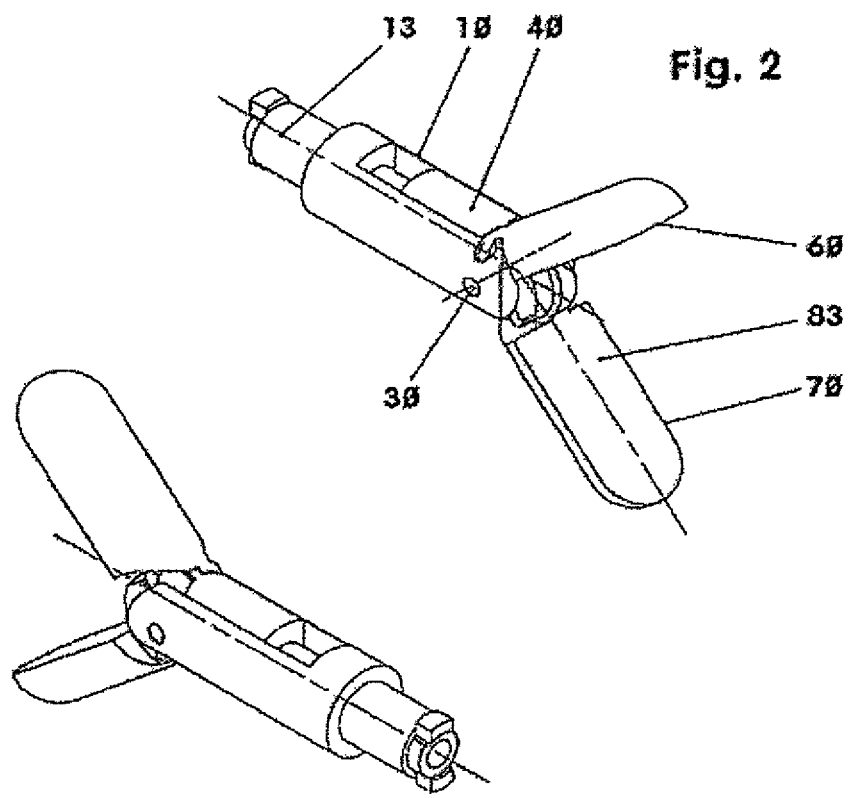
Fig. 2
Fig. 3

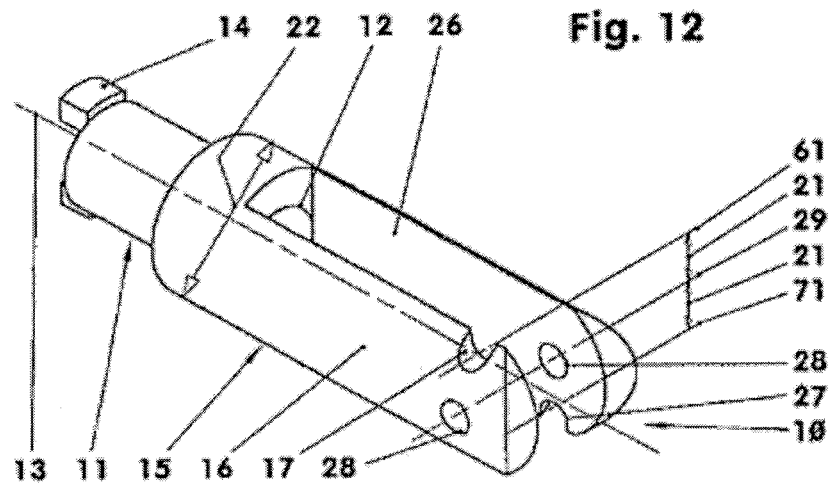
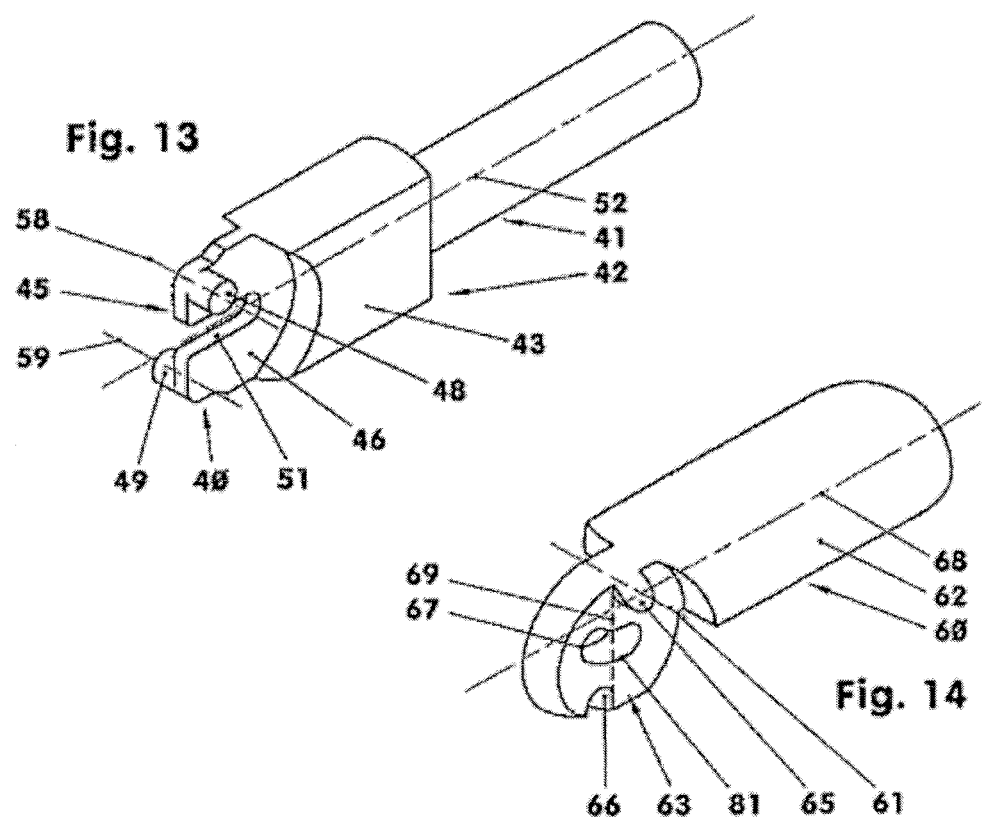

SURGICAL GRIPPING FORCEPS

CROSS REFERENCE TO RELATED APPLICATIONS

This application claims priority from Ser. No. PCT/EP2007/007412 filed Aug. 23, 2007, the entire contents of which are herein incorporated by reference. This application in turn claims priority from DE App. Ser. No. 10 2006 040 5293 filed on Aug. 30, 2006.

BACKGROUND OF THE INVENTION

1. Field of the Invention

The invention relates to a surgical gripping forceps with two gripping jaws movable relative to a main body, wherein each gripping jaw has a pivot pin, fixed in position relative to the main body, and a lever arm, and wherein the lever arms are articulated via at least one push element.

2. Description of the Related Art

Laparoscopic surgery requires a special set of instruments. What all the instruments have in common is miniaturization, for which reason laparoscopic surgery is also known as endoscopic microsurgery. The instruments are introduced into the abdomen through long sleeves having a diameter generally between four and twelve millimeters, usually via Torkar sleeves, and they are operated with manual force outside the abdominal cavity.

In microsurgery, one needs to have both fine gripping instruments for the preparation and also large ones for the extraction of resected organs. Various gripping instruments with a diameter of three, five or ten millimeters are available. On the one hand there are atraumatic forceps and on the other hand toothed forceps. They have gripping jaws that are pointed or broad, fine or large. Sometimes the gripping instruments also have locking mechanisms.

The gripping forceps must be simple and safe to use. This includes a transmission of manual force by the gripping forceps mechanism. It is also advantageous for the gripping forceps, that is, the part which extends out from the Torkar sleeve in the abdomen, to have the fewest parts possible. Few parts always means few movable joints. This lowers the risk of injury and facilitates the disinfecting of the gripping forceps. The latter holds only when the particular forceps is not a disposable kind.

A convention gripping forceps is known from U.S. Pat. No. 5,342,390, the entire contents of which are herein incorporated fully by reference. The gripping jaws of this forceps are mounted on a shared pivot pin. The pivot pin intersects the center line of the main body of the forceps. As a result, and as a detriment, the lever arms formed on the gripping jaws and moved via the gripping jaws are necessarily only relatively short in configuration. As an additional detriment, a separate push element acts on each lever arm of the gripping jaws.

ASPECTS AND SUMMARY OF THE INVENTION

One aspect of the present invention proposes a solution that overcomes at least one of the detriments noted above.

Another aspect of the present invention is to develop a surgical gripping forceps which, with a customary force for actuating the forceps, enables a substantial clamping force of the forceps between the gripping jaws while also minimizing the number of structural parts for a forceps of small size.

In another aspect of the present invention, a solution is provided wherein at least one and preferably each gripping jaw has its own pivot pin. The individual pivot pin has at least a distance from the center line of the main body greater than 38% of the maximum width of the main body or maximum diameter of the main body.

In one aspect of the present invention surgical gripping forceps are provided with one or two gripping jaws movable relative to a main body, wherein each moveable one of the gripping jaws has a pivot pin, fixed in position relative to the main body, and a lever arm. The lever arms are articulated via at least one push element. For this purpose each movable one of the gripping jaws has its own pivot pin. From the midline of the main body, the individual pivot pin has at least a distance greater than 38% of the maximum width of the main body or maximum diameter of the main body. The microsurgical gripping forceps operate with customary force for actuating the forceps, and permit a substantial applied clamping force.

According to another alternative aspect of the present invention, there is provided a surgical gripping forceps apparatus, said apparatus comprising: (a) a main body; and (b) at least two gripping jaws extending outwardly from said main body, wherein at least one of said gripping jaws is movably arranged relative to said main body, and wherein said at least one movable gripping jaw further comprises: (i) a pivot pin, fixed in position relative to said main body, said pivot pin having at least a distance from a center line of said main body greater than thirty-eight percent (38%) of one of the maximum width of said main body and a maximum diameter of said main body; and (ii) a lever arm, wherein said lever arm is articulated via at least one push element.

According to another alternative aspect of the present invention, there is provided a forceps apparatus, the apparatus comprising: a main body, the main body further comprising: (a) a tube segment, the tube segment comprising: (i) a central bore in which a push element is guided therethrough, (ii) a housing tube, and (iii) a plurality of adapter elements located at a rear end of the tube segment and further situated in a fixed relationship to each one of the plurality of adapter elements, and wherein the main body is detachably fastened to the housing tube, and (b) a fork segment, the fork segment having at least two fork arms, each of the fork arms are arranged on the tube segment and capable of gripping an object under direction of an apparatus user, and (c) wherein the main body is detachably fastened to the housing tube by means of a quarter-turn fastener.

According to another aspect of the present invention, there is provided a surgical gripping forceps apparatus, the apparatus comprising: (a) a main body, and (b) at least two gripping jaws extending outwardly from the main body, wherein at least one of the gripping jaws is movably arranged relative to the main body, and wherein the at least one movable gripping jaw further comprises: (i) a pivot pin, fixed in position relative to the main body, the pivot pin having at least a distance from a center line of the main body greater than thirty-eight percent of the maximum width of the main body or a maximum diameter of the main body, and (ii) a lever arm, wherein the lever arm is articulated via at least one push element, and (c) a push element in the main body, the push element capable of articulating one or more of each of the movable gripping jaws.

The above, and other aspects, features and advantages of the present invention will become apparent from the following description read in conduction with the accompanying drawings, in which like reference numerals designate the same elements.

BRIEF DESCRIPTION OF THE DRAWINGS

FIG. 1 is a perspective left front view of a closed gripping forceps according to one aspect of the present invention.

FIG. 2 is a perspective right front view of an open gripping forceps.

FIG. 3 is a perspective rear view of FIG. 2.

FIG. 12 is a front perspective view of a main body member.

FIG. 13 is a front perspective view of a push element.

FIG. 14 is a front perspective view of a gripping jaw member.

DETAILED DESCRIPTION OF THE PREFERRED EMBODIMENTS

Figure 4:
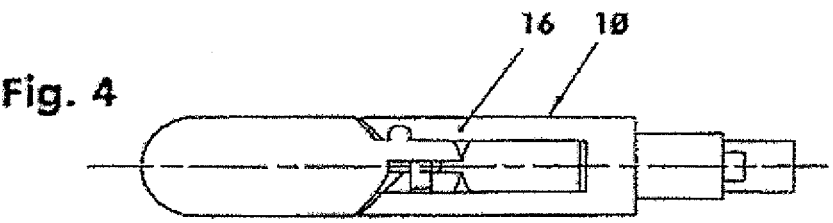
FIG. 4 is a top plan view of a gripping forceps.

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, and below may be used with respect to the drawings. These and similar directional terms should not be construed to limit the scope of the invention in any manner. The words "connect," "couple," and similar terms with their inflectional morphemes do not necessarily denote direct and immediate connections, but also include connections through mediate elements or devices.

Referring now to FIGS. 1-3 a surgical gripping forceps in closed and opened views are presented. The gripping forceps comprises a main body 10, a push element 40 (having center line 13), two gripping jaws 60, 70, and a guide bolt 30.

The main body 10, also see FIG. 12, consists of a tube segment 11 and a fork segment 15. The tube segment 11 has a central bore 12, in which the push element 40 is guided. At its rear end, two adapter elements 14 situated opposite each other are formed. By these adapter elements 14, the main body 10 is fastened to a housing tube (not shown) in detachable manner, e.g., by means of a quarter-turn fastener.

The fork segment 15 has two fork arms 16, 26, which are arranged on the tube segment 11. The outer walls of the fork arms 16, 26 are, for example, parts of a cylindrical shell. The diameter of this cylinder is the diameter 22 of the main body. In the sample embodiment, it amounts to 4.8 mm. The inner walls of the fork arms 16, 26 are planes lying parallel to each other. The spacing between the planes corresponds, e.g., to the inner diameter of the central bore 12. At their front ends, the fork arms 16, 26 each have a bore 28. The bores 28, aligned with each other, have a center line 29 that intersects perpendicularly the center line 13 of the main body 10.

The front fork arm 16 per FIG. 12 has a groovelike recess 17, of U shape for example, above the bore 28. The bottom of the recess has partially the surface of a cylindrical shell. The center of the cylindrical shell is an upper pivot axis 61. The rear fork arm 26 has a comparable recess 27. The latter is oriented downward here and partially encloses a lower pivot axis 71. The pivot axes 61, 71 and the center line 29 of the bores 28 lie in the same plane. This plane is oriented normal to the center line 13 of the main body 10.

FIG. 13 shows the push element 40. It consists of a push pin segment 41, a guide segment 42 and a bearing segment 45. The push pin segment 41, by which the push element 40 is mounted in the main body 10, has a cylindrical shape. At its free end it can have a threaded bore. Then, in the latter, the actuating rod led through the housing tube of the forceps is detachably secured. The threaded bore, the housing tube, and the actuating rod are not shown in the figures.

After the push pin segment 41 comes the guide segment 42. The latter has at least approximately the shape of a cuboid, similar to that shown, with two plane side surfaces 43 parallel to each other. In the assembled gripping forceps, these side surfaces 43 lie against the inner walls of the fork arms 16, 26 of the main body 10. Here, they have the function of twist prevention, among other things. The curved partially cylindrical surfaces which adjoin the side surfaces 43 at top and bottom belong to a cylinder whose diameter corresponds to the diameter of the main body.

The guide segment 42 passes into a bearing segment 45. The bearing segment 45 corresponds to a thin-wall plate, which has two link pins 48, 49 and a guide groove 51. The link pins 48, 49 have center lines 58, 59 parallel to each other. The two center lines 58, 59 subtend a plane that lies normal to the center line 52 of the push element 40. The upper link pin 48 per FIG. 13 is oriented in front, while the lower one 49 is facing the rear. The two link pins 48,49 have the same distance from the center line 52. The distance 21 between the center lines 58, 59 is more than ⅔ of the diameter 22 of the main body. The link pins 48, 49 have a diameter e.g., of 1 mm (millimeter).

In the middle between the link pins 48, 49 is a straight guide groove 51, which is open at the free end of the bearing segment 45. The closed end of the guide groove 51 has a partially cylindrical rounding. The center line of the rounding intersects the center line 52 of part 40 perpendicularly.

FIG. 14 shows one of two gripping jaws 60. It is the upper gripping jaw in spatial relation to the parts 10 and 40 shown in FIGS. 12 and 13. The gripping jaw 60 consists of a jaw segment 62 and a pivot region segment 63. The jaw segment 62 has the shape of half of a longitudinally divided cylinder. The diameter of this cylinder coincides with the diameter 22 of the main body. The front free end of the jaw segment 62 is rounded. The radius of the rounding corresponds to half the diameter 22 of the main body.

The pivot region segment 63, at least approximately in the shape of a circular disk, extends in the front half of the gripping jaw 60. That is, the rear plane surface of the pivot region segment 63—contacted by a bearing surface 46 of the bearing segment 45 of the push element 40—lies in a plane which is half the width of the bearing segment 45 away from the central plane of the structural parts. The center line 68 of the structural part runs in this plane of centers. Also on this line lies the atraumatic jaw gripping surface 83, which is flat here, see FIG. 2.

In the upper region, the pivot region segment 63 has a forward extending pivot pin 65. The pivot pin 65, which has a center line 61, has a cylindrical outer contour, at least at the bottom. Beneath the pivot pin 65 is a crescent-shaped guide cavity 67. The radius of curvature of the guide cavity 67 has a center point which lies on the center line 61 of the pivot pin 65. Consequently, the guide cavity 67 has at least one circular arc edge 81 whose center point likewise lies on the center line 61. Beneath the guide cavity 67, a link cavity 66 is produced in the pivot region segment 63 at the bottom. For example, the link cavity 66 is a straight groove, whose width is slightly larger than the diameter of the link pins 48, 49 of the push element 40. The bottom of the cavity here as well as the surface of a cylindrical shell in part.

In FIG. 14, an accessory dashed line 69 has been drawn on the visible plane surface which lies against the inner wall of the respective fork arm 16, 26 of the main body 10 when the gripping forceps is assembled. The accessory line 69, furthermore, is perpendicular to the plane of the jaw gripping surface 83. On this accessory line 69 lie the front contour line of the pivot pin 65 and the edge of the rear flat wall of the link cavity 66.

The fifth and last structural part of the gripping forceps is the cylindrical guide bolt 30, see FIG. 2. Its diameter in the sample embodiment is 1 mm. Its length is slightly less than the main body diameter 22. It sits in the bores 28 of the gripping arms 16, 26, for example, by means of a transverse press fit.

All five parts 10, 30, 40, 60, 70 of the gripping forceps are made from a stainless or acid resistant steel, for example, such as chromium steel X20Cr13.

Before explaining the interaction of the parts of the forceps, the functional principle shall be briefly discussed. The functional principle is represented in FIGS. 5 and 6, at first for only one gripping jaw 60.

Figure 5:
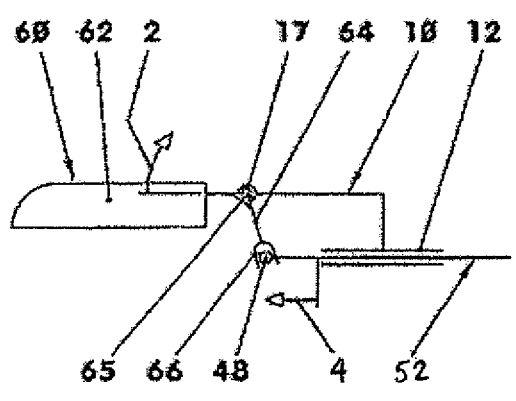
FIG. 5 is a schematic side view of half the gripping forceps in a closed position.
Figure 6:
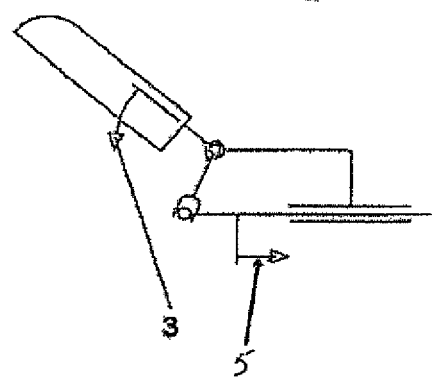
FIG. 6 is a schematic side view of half the gripping forceps in an open position.

According to FIG. 5, the gripping jaw 60 is a jaw segment 62 on which a lever arm 64 is fastened by a link cavity 66 and a pivot pin 65. The main body 10 is a straight guideway 12 with a pivot pin bearing 17 arranged thereon. The push element 40 is mounted in the straight guideway 12. This engages with the link cavity 66 via a link pin 48.

To open the gripping jaw 60, the push element 40 is pushed to the left 4 into the straight guide 12. The link pin 48 acts on the link guideway 66. This along with the lever arm 64 and the jaw segment 62 swivels upward in the clockwise direction 2. At the same time, the pivot pin 65 rotates in the pivot pin bearing 17 of the main body 10. To close the gripping jaw 60, the push element 40 is pushed to the right 5 out from the straight guide 12 such that the jaw segment 62 swivels downward in the counter-clockwise direction 3, see FIG. 6. Similar actions effect movement of corresponding jaw segment 72, which has a forward extending pin 75, link 74 and link cavity 76 at its rear end portion.

Figure 7:
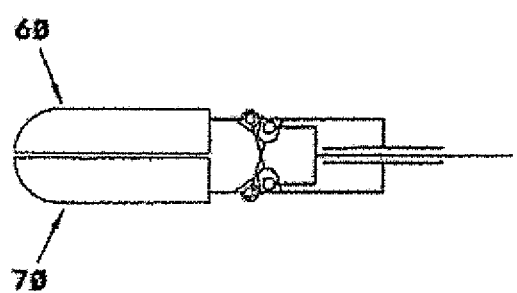
FIG. 7 is a schematic side view of the whole closed gripping forceps.
Figure 8:
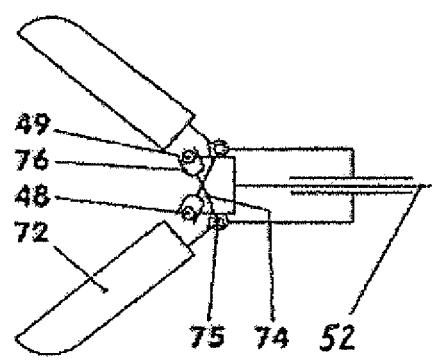
FIG. 8 is a schematic side view of the whole open gripping forceps.

The principle for the overall gripping forceps is shown in FIGS. 7 and 8. For this, the sketches presented in FIGS. 5 and 6 are first shown mirrored at the bottom. Then original and mirror image are pushed together until the gripping jaws 60, 70 per FIG. 4 lie against each other. Now, to make do with a single straight guideway 12, both link pins 48, 49 are firmly arranged on a shared push element 40.

Figure 9:
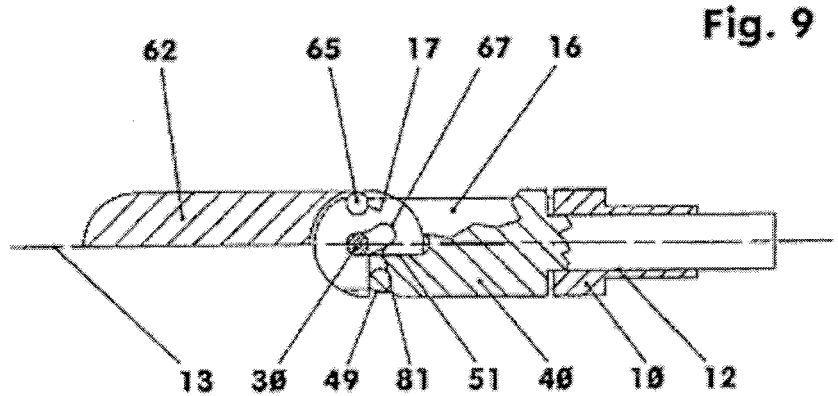
FIG. 9 is a partial sectional top view of a gripping forceps with only one gripping jaw in a closed position.

The individual parts 10, 30, 40, 60, 70 of the actual gripping forceps, see FIGS. 12 to 14, are mounted by shoving the push element 40 with its guide segment 42 almost completely forward along center line 52 into the bore 12 of the main body 10. The depth of insertion is shown in FIG. 9. Now, the upper gripping jaw 60 is inserted from the top into the gap between the front fork arm 16 and the bearing surface 46 of the push element 40. The gripping jaw 60 is now in the extended position, i.e., its center line 68 runs parallel to the center line 13 of the main body 10 during the insertion process. During the downward movement, the pivot pin 65 of the gripping jaw 60 comes to rest in the cavity 17 of the main body 10. At the same time, the link cavity 66 of the gripping jaw 60 is pushed via the link pin 49 of the push element 40. The inserting of the gripping jaw 60 is finished once the center line 68 of the gripping jaw 60 coincides with the center line 13 of the main body 10. The lower gripping jaw 70 is inserted from the bottom in comparable manner.

In this arrangement of the structural parts, five cavities or bores lie at least partially superimposed in the link region of the gripping forceps. These are—looking in from the outside—the two bores 28 of the fork arms 16, 26, the two crescent-shaped guide cavities 67, 77 of the gripping jaws 60, 70, and the guide groove 51 of the push element 40. Finally, the guide bolt 30 is inserted through all cavities and secured, see FIG. 1 to 4.

Figure 10:
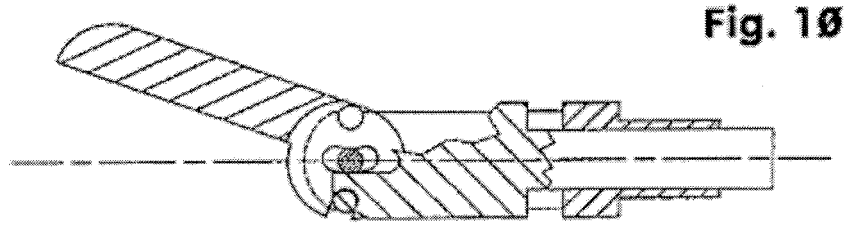
FIG. 10 is a partial sectional top view of a gripping forceps as in FIG. 9, in a half-open position.
Figure 11:
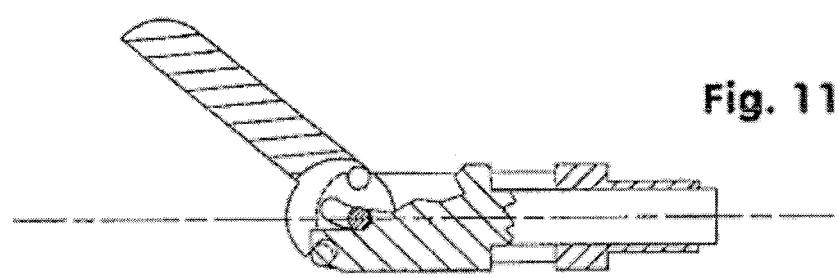
FIG. 11 is a partial sectional top view of a gripping forceps as in FIG. 10, in a fully open position.

The function of the crescent-shaped cavity 67 of the gripping jaw 60, not yet described, shall be explained in FIG. 9 to 11. In these figures, the gripping forceps is shown in longitudinal section without the lower gripping jaw 70. Furthermore, a piece has been broken off from the push element 40.

The main body 10 supports the gripping jaw 60 in the cavity 17 and on the guide bolt 30. The pivot pin 65 lies in the cavity 17, which is open to one side. The crescent-shaped guide cavity 67 encloses the guide bolt 30. Now, to prevent an unintentional upward movement of the pivot pin 65 or gripping jaw 67, the guide cavity 66 lies against the guide bolt 30 at least via the edge 81. Thanks to the abutment of the guide cavity 67 against the guide bolt 30, it is possible to situate the pivot axis 61 of the gripping jaw 60 far from the center line 13 inside the main body 10. This enables a large lever arm for the gripping forceps.

Figure 15:
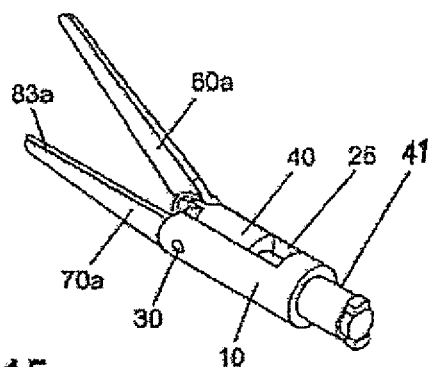
FIG. 15 is a perspective view of an alternative embodiment of a gripping forceps according to the present invention.
Figure 16:
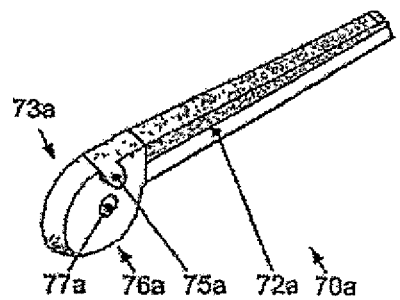
FIG. 16 is a partial member of a gripping forceps embodiment as in FIG. 15.
Figure 17:
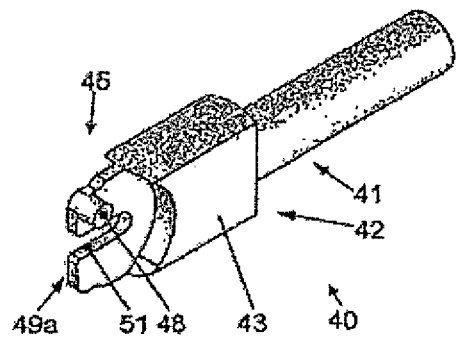
FIG. 17 is a perspective view of a pushing element according to FIG. 15.

FIGS. 15 to 17 show a surgical gripping forceps in another modified configuration in opened representation. For this configuration, basically only the differing features will be described, making reference to FIG. 1 to 14 and then description. The same reference numbers in the figures designate the same or identically acting elements and the numbers with an "a" designate differing elements.

The gripping forceps likewise comprises a main body 10, a push element 40, two gripping jaws 60a, 70a and a guide bolt 30. However, only one of the gripping jaws 60a is mounted movable in the main body 10 by means of a guide bolt 30. The other of the gripping jaws 70a, on the other hand, is inserted stationary in the main body 10 or forms a single piece with the latter.

FIG. 16 shows the nonmovable one of the gripping jaws 70a. The lower gripping jaw is in spatial relation to the structural parts 10 and 40 represented in FIGS. 15 and 17. The nonmovable gripping jaw 70a likewise consists of a jaw segment 72a, but instead of a pivot region segment it has a modified rear segment 73a. The jaw segment 62 in this configuration has the shape, for example, of an elongated ridge or a broadened blade.

The rear segment 73a extends in the front half of the gripping jaw 70a, as in the first embodiment. That is, the back plane surface of the rear segment 73a makes contact with a bearing surface of the bearing segment of the push element 40 and lies in a plane away from the plane of centers of the structural parts, especially by half the width of the bearing segment. The center line of the structural part lies in this plane of centers. The atraumatic jaw gripping surface 83a, which is likewise flat here, also lies on this line (FIG. 15).

In the upper region, the rear segment 73a has a forward extending pin 75a similar to the pivot pin of the first embodiment. The pin 75a, which has a center line similar to center line 58 shown in FIG. 13, has an outer cylindrical contour at least at the bottom. Beneath the pin 75a is a cylindrical cavity 77a, instead of a crescent-shaped guide cavity. The cylindrical cavity 77a sits on the guide bolt 30 (FIG. 15). Due to this configuration, the lower gripping jaw 70a is inserted in the main body 10 so that it cannot move or pivot.

Alternatively, one could also use a main body 10 forming a single piece with such a gripping jaw 70a.

FIG. 17 shows a modified push element 40. Again, it consists of a push pin segment 41, a guide segment 42 and a bearing segment. The push pin segment 41 adjoins the guide segment 42. The latter, again, has the shape of a cuboid, for example, with two plane side surfaces 43 parallel to each other. The guide segment 42 passes into a front bearing segment 45.

The bearing segment 45 again corresponds to a thin-wall plate, for example, having in this configuration a guide groove 51 but only one such link pin 48. In other words, there is no link pin 49a on the opposite side, which would have served to operate the stationary gripping jaw 70a. Accordingly, no link cavity 76a is required at the bottom in the gripping jaw 70a, contrary to the corresponding gripping jaw in the rear segment 73a beneath the cavity 77a.

The invention claimed is:

1. A surgical gripping forceps apparatus, said apparatus comprising:
   (a) a main body comprising a fork segment with two fork arms; and
   (b) at least two separate gripping jaws extending outwardly from said main body, wherein each of said gripping jaws is movably arranged relative to said main body, and wherein said movable gripping jaws each further comprise a pivot pin extending sidewardly fixed in position relative to said main body, said pivot pin having at least a distance from a common central line extending lengthwise through said main body greater than thirty-eight percent (38%) of the maximum width of said main body; and
   (c) a lever arm articulating each separate said gripping jaw via at least one separate push element extending from opposing sides of said lever arm.

2. The surgical gripping forceps apparatus in accordance with claim 1, wherein each of said gripping jaws extends outward from, and is movably arranged relative to, said main body, each of said gripping jaws comprising:
   (a) a pivot axis fixed in place relative to said main body, said pivot axis having a distance from said common central line of said main body at least more than thirty-eight percent (38%) of said maximum width of said main body; and
   (b) a lever arm articulated via said at least one push element.

3. The surgical gripping forceps apparatus in accordance with claim 2, wherein each of said pivot axes for each of a corresponding movable gripping jaw is arranged parallel to each other of said axes.

4. The surgical gripping forceps apparatus in accordance with claim 2, wherein said pivot axis of each of said movable gripping jaws lies in a plane oriented normal to said central line of said main body.

5. The surgical gripping forceps apparatus in accordance with claim 2, wherein said pivot axis of each of said movable gripping jaws is formed by a respective pivot pin at a corresponding side of said gripping jaw and a cavity at a side of said main body.

6. The surgical gripping forceps apparatus in accordance with claim 5, wherein said cavity at said main body side only partly encloses each respective said pivot pin at said corresponding side of said gripping jaw.

7. The surgical gripping forceps apparatus in accordance with claim 5, wherein each of said movable gripping jaws comprises:
   a guide cavity proximate said pivot pin, and wherein said guide cavity has at least one curved edge forming a circular arc about said pivot axis of said pivot pin.

8. The surgical gripping forceps apparatus in accordance with claim 7, wherein said edge of said guide cavity is braced against a guide bolt mounted in said main body.

9. The surgical gripping forceps apparatus in accordance with claim 1, and wherein:
   at least one of said push elements capable of articulating one or more of each of said movable gripping jaws.

10. The surgical gripping forceps apparatus in accordance with claim 9, wherein said push elements are configured to be guided by said main body in at least two directions.

11. The surgical gripping forceps apparatus in accordance with claim 1, wherein said main body and said push element form a sliding pair, and wherein said push element is non-twistably mounted in said main body.

12. The surgical gripping forceps apparatus in accordance with claim 1, wherein said main body, said push element, and said gripping jaws form at least one rocking slider crank, an individual link cavity of each of said slider cranks being each arranged on a lever arm of a respective movable one of said gripping jaws.

13. The surgical gripping forceps apparatus in accordance with claim 1, and further comprising:
   a push element in said main body, said push element capable of articulating one or more of each of said movable gripping jaws; and
   wherein said push element is configured to be guided by said main body in at least two directions within a bore of said main body and between fork arms of said main body.

14. The surgical gripping forceps apparatus in accordance with claim 1, wherein each of said gripping jaws extends outward from, and is movably arranged relative to, said main body, each of said gripping jaws comprising:
   (a) a pivot axis fixed in place relative to said main body, said pivot axis having a distance from said common central line of said main body at least more than thirty-eight percent (38%) of a maximum width of said main body; and
   (b) a lever arm articulated via at least one push element;
   wherein said pivot axis of each of said movable gripping jaws is formed by a pivot pin at a corresponding side of said gripping jaw and a cavity at a side of said main body; and
   wherein said cavity at said main body side only partly encloses said pivot pin at said corresponding side of said gripping jaw.

15. The surgical gripping forceps apparatus in accordance with claim 1, wherein each of said gripping jaws extends outward from, and is movably arranged relative to, said main body, each of said gripping jaws further comprising:
(a) a pivot axis fixed in place relative to said main body, said pivot axis being a distance from said common central line of said main body at least thirty-eight percent of a maximum width of said main body; and
(b) a lever arm being articulated via at least one push element;
wherein said pivot axis of each of said movable gripping jaws is formed by a pivot pin extending outwardly at a corresponding side of said gripping jaw and a respective cavity at a side of said main body; and
wherein at least one of said movable gripping jaws comprises:
a guide cavity proximate said push element, wherein said guide cavity has at least one curved edge forming a circular arc about a pivot axis of said push element, and said edge of said guide cavity is braced against a guide bolt mounted in said main body.

16. A forceps apparatus, said apparatus comprising:
a main body, said main body further comprising:
(a) a tube segment, said tube segment comprising:
(i) a central bore in which a push element is slidably guided therethrough to effect actuation of the forceps apparatus; and
(ii) a plurality of adapter elements located at a rear end of said tube segment, said adapter elements being situated in a fixed relationship to one another about outer portions of said tube segment, and wherein said main body is capable of being detachably fastened to a housing tube;
(b) a fork segment having at least two fork arms, each of said fork arms being arranged extending parallel from said tube segment; and
a pair of gripping jaws connected to and extending outwardly from said main body, wherein said gripping jaws are movably arranged relative to said main body and a lever arm, and wherein said two movable gripping jaws each further comprises a pivot pin extending sidewardly on opposing sides thereof and fixed in position relative to said main body, said gripping jaws capable of gripping an object under direction of an apparatus user; and
a lever arm articulating each separate said gripping jaw via at least one separate push element extending from opposing sides of said lever arm.

17. The forceps apparatus in accordance with claim 16, wherein each of said gripping jaws extends outward from, and is movably arranged relative to, said main body, each of said gripping jaws comprising:
(a) a pivot axis fixed in place relative to said main body, said pivot axis having a distance from a common central line extending lengthwise through said main body at least thirty-eight percent of a maximum width of said main body.

18. The surgical gripping forceps apparatus in accordance with claim 17, wherein said main body, said push element, and said gripping jaws form at least one rocking slider crank, wherein an individual link cavity of each of said at least one slider crank is arranged on a lever arm of a respective movable one of said gripping jaws.

19. A surgical gripping forceps apparatus, said apparatus comprising:

(a) a main body comprising a fork segment;
(b) said fork segment comprising two fork arms;
(c) each of said two fork arms having a central bore aligned with each other and providing a common central line extending lengthwise through the main body and between said two fork arms;
(d) a first of said two fork arms having a recess above said bore and a second of said two forks arms having a recess below said bore;
(e) at least two gripping jaws extending outwardly from said main body, wherein both of said gripping jaws are movably arranged relative to said main body, and wherein said two movable gripping jaws each further comprises:
(i) a fixed pivot pin extending sidewardly and lying in the respective recess of a fork arm; and
(ii) a link cavity beneath said pivot pin;
(f) a lever arm having a plurality of link pins directed outwardly on opposing sides of the lever arm in opposite directions, a first of said link pins being arranged to fit in a link cavity of the first gripping jaw and a second of said link pins of the lever arm being arranged to fit in a link cavity of the second gripping jaw.

20. A surgical gripping forceps apparatus, said apparatus comprising:
(a) a main body comprising a fork segment with two fork arms; and
(b) at least two gripping jaws extending outwardly from said main body, wherein said gripping jaws are movably arranged relative to said main body, and wherein said two movable gripping jaws each further comprises:
(i) a pivot pin extending sidewardly fixed in position relative to said main body, said pivot pin having at least a distance from a line extending lengthwise therethrough said main body at a position greater than thirty-eight percent (38%) of a maximum width of said main body;
(ii) a lever arm articulated via at least one push element; and
(c) a guide cavity proximate said pivot pin, wherein said guide cavity has at least one curved edge forming a circular arc about said pivot axis of said pivot pin, and said edge of said guide cavity is braced against a guide bolt mounted in said main body;
wherein said pivot axis of each of said movable gripping jaws is formed by said pivot pin at a corresponding side of said gripping jaw and said cavity at a side of said main body.

21. The surgical gripping forceps apparatus, in accordance with claim 20, wherein at least one of said gripping jaws is non-movable relative to said main body.

22. The surgical gripping forceps apparatus in accordance with claim 20, wherein said main body and said push element form a sliding pair, and wherein said push element is non-twistably mounted in said main body.

23. The surgical gripping forceps apparatus in accordance with claim 20, wherein said main body, said push element, and said gripping jaws form at least one rocking slider crank, an individual link cavity of each of said at least one slider crank being each arranged on said lever arm of a respective movable one of said gripping jaws.

* * * * *